(12) United States Patent
Kuboki et al.

(10) Patent No.: US 12,741,120 B2
(45) Date of Patent: Sep. 22, 2026

(54) CATHETER

(71) Applicant: Asahi Intecc Co., Ltd., Seto (JP)

(72) Inventors: Teppei Kuboki, Seto (JP); Keiichi Fujino, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 701 days.

(21) Appl. No.: 18/098,135

(22) Filed: Jan. 18, 2023

(65) Prior Publication Data

US 2023/0149662 A1 May 18, 2023

Related U.S. Application Data

(63) Continuation of application No. PCT/JP2020/028761, filed on Jul. 27, 2020.

(51) Int. Cl.
*A61M 25/01* (2006.01)
*A61M 25/00* (2006.01)

(52) U.S. Cl.
CPC ........ *A61M 25/01* (2013.01); *A61M 25/0041* (2013.01); *A61M 25/0053* (2013.01); *A61M 25/0054* (2013.01); *A61M 25/0045* (2013.01); *A61M 2205/0216* (2013.01)

(58) Field of Classification Search
CPC .............. A61M 25/01; A61M 25/0054; A61M 25/0041; A61M 25/0053; A61M 25/0045; A61M 2205/0216; A61M 25/0067; A61M 25/0068; A61M 25/008
See application file for complete search history.

(56) References Cited

U.S. PATENT DOCUMENTS 4,508,535 A * 4/1985 Joh ..................... A61M 60/196 604/174
5,800,413 A * 9/1998 Swartz .............. A61M 25/0041 604/528

(Continued)

FOREIGN PATENT DOCUMENTS

JP 2001-87389 A 4/2001
JP 2003038656 A 2/2003
JP 2003-190289 A 7/2003

(Continued)

OTHER PUBLICATIONS

International Search Report and Written Opinion mailed on Oct. 6, 2020, received for PCT Application PCT/JP2020/028761, filed on Jul. 27, 2020, 8 pages including English Translation.

*Primary Examiner* — Catherine S Williams
(74) *Attorney, Agent, or Firm* — XSENSUS LLP

(57) ABSTRACT

A catheter, including: a hollow shaft having a distal end that includes a first section extending substantially linearly and a second section on a distal end side of the first section. The second section includes a first curved region and a second curved region, less rigid than the first curved region, on the more distal end side than the first curved region. A virtual plane on the axis of the hollow shaft forms a boundary, and spaces on both sides of the virtual plane define a first area and a second area. The first curved region and the distal end of the catheter are in the first area. The second curved portion is in the second area. A distance from the distal end of the catheter to the virtual plane is larger than a distance from the first curved portion to the virtual plane.

16 Claims, 6 Drawing Sheets

(56) References Cited

U.S. PATENT DOCUMENTS

| | | | | |
|---|---|---|---|---|
| 6,511,462 | B1 | 1/2003 | Itou et al. | |
| 2006/0089618 | A1* | 4/2006 | McFerran | ......... A61M 25/0068<br>604/525 |

FOREIGN PATENT DOCUMENTS

| | | | | |
|---|---|---|---|---|
| JP | 2008-517652 | A | 5/2008 | |
| JP | 2010-508910 | A | 3/2010 | |
| JP | 2012-29872 | A | 2/2012 | |
| JP | 2018-515210 | A | 6/2018 | |
| WO | WO-2007035554 | A1 * | 3/2007 | ......... A61B 18/1492 |
| WO | 2008/058019 | A2 | 5/2008 | |
| WO | WO-2016191062 | A2 * | 12/2016 | ........ A61M 25/0041 |
| WO | WO-2022024201 | A1 * | 2/2022 | ............ A61M 25/01 |

* cited by examiner 1
10
11
12
13
14
15
21
22
23
31
32
40
51
52
60
70
71
72
73
p1
p2
D1
D2
D3

FIG.2

51
52
1
10
11
14
12
D1
40
Rmax1
α1
p1
31
C1
A1
Rc1
15
13
α2
Rc2
A2
C2
p2
60
Rmax2
32
D3
D2

1
120
11
10
102
14
120
12
101
31
15
120
100
60
120
32
13

CATHETER

CROSS-REFERENCE TO RELATED APPLICATION

This application is a continuation application of International Application No. PCT/JP2020/028761 filed Jul. 27, 2020, the entire contents of which is incorporated herein by reference.

TECHNICAL FIELD

The disclosed embodiments relate to a catheter.

BACKGROUND ART

Conventionally, there is known a catheter including a hollow shaft with a curved distal end portion (Patent Literature 1, for example).

CITATION LIST

Patent Literature

Patent Literature 1: JP 2001-87389 A

SUMMARY

Technical Problems

However, the above-described prior art still has room for improvement in technology of enhancing the performance (selectivity) for advancing a catheter to a target direction in complicatedly branching internal organs and blood vessels.

Disclosed embodiments aim at enhancing the performance (selectivity) for advancing a catheter to a target direction in complicatedly branching internal organs and blood vessels.

Solutions to Problems

Disclosed embodiments have been made to solve at least a part of the problems described above, and can be realized as the following aspects.

(1) According to one aspect of the disclosed embodiments, a catheter is provided. The catheter is a catheter including a hollow shaft, in which a distal end portion of the hollow shaft includes a first section extending substantially linearly, a second section connected to a distal end side of the first section and provided with a first curved portion, and a third section connected to a distal end side of the second section and provided with a second curved portion, the rigidity of the second section is larger than the rigidity of the third section, with a virtual plane set along an axis of the first section, a space area on one side with respect to the virtual plane being a first area, and a space area on the other side being a second area, the first curved portion and a distal end of the catheter are positioned in the first area, the second curved portion is positioned in the second area, and a distance from the distal end of the catheter to the virtual plane is larger than a distance from the first curved portion to the virtual plane.

With this configuration, force applied in the axial direction of the catheter, such as the force for pushing in the catheter, is converted to the distal end direction of the catheter through the first curved portion and the second curved portion. Thus, the catheter easily advances toward the distal end direction of the catheter. Moreover, the distance from the distal end of the catheter to the virtual plane is larger than the distance from the first curved portion to the virtual plane. Thus, when the distal end of the catheter reaches a branching portion of a blood vessel, the distal end of the catheter is easily inserted to the branching portion. Furthermore, the rigidity of the second section is larger than the rigidity of the third section. Thus, the possibility that the distal end of the catheter is pushed back to the rear end side of the catheter may be reduced.

(2) In the catheter of the above-described aspect, the rigidity of the first section of the hollow shaft may larger than the rigidity of the second section. With this configuration, the force for pushing in the catheter, the force for rotating the catheter, and the like, may be securely transmitted from the rear end side of the catheter to the distal end side of the catheter.

(3) In the catheter of the above-described aspect, in a front view of the catheter, a distal end of the first section, a distal end of the first curved portion, and a distal end of the second curved portion in the hollow shaft are arranged on a straight line.

In a front view of the catheter, the distal end of the first section, the vertex of the first curved portion, and the vertex of the second curved portion may be arranged on a straight line. With this configuration, as compared with the case where the distal end of the first section, the vertex of the first curved portion, and the vertex of the second curved portion are not arranged on a straight line, the possibility that force in a direction orthogonal to the axial direction of the catheter occurs, is reduced, thereby reducing the possibility that the distal end portion of the catheter rotates in a direction not intended by a user.

Note that the disclosed embodiments can be achieved in various aspects, such as a guide wire, a method for producing a guide wire, a method for producing a catheter, an endoscope, and a dilator, for example.

BRIEF DESCRIPTION OF THE DRAWINGS

FIG. 2 is an explanatory view illustrating curved portions of the catheter according to the first embodiment.

DESCRIPTION OF EMBODIMENTS

First Embodiment

Figure 1:
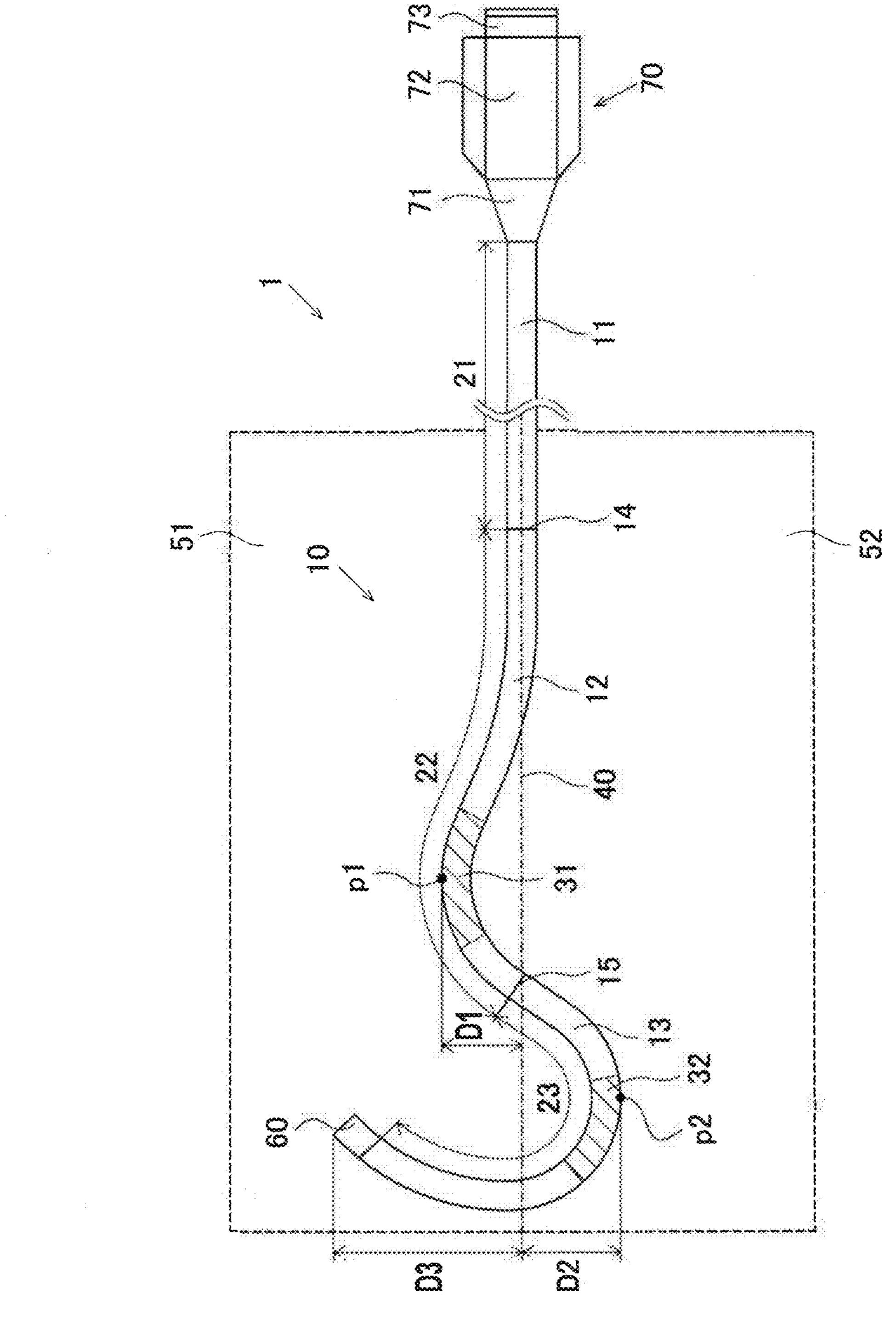
FIG. 1 is an explanatory view illustrating the entire configuration of a catheter according to a first embodiment.

FIG. 1 is an explanatory view illustrating the entire configuration of a catheter 1 according to the first embodiment. In FIG. 1, the relative ratio of the sizes of the components is partially different from the actual ratio, for convenience of description. The same applies to the explanatory views illustrated in FIG. 2 to FIG. 6.

In FIG. 1, the left side is the distal end side of the catheter 1 and of each component of the catheter 1, while the right side is the rear end side of the catheter 1 and of each component of the catheter 1. The distal end side of the catheter 1 is the side (far side) to be inserted into a body, and the proximal end side of the catheter 1 is the side (near side) to be operated by a technician such as a physician. The right and left direction of FIG. 1 is referred to as an axial direction of the catheter 1 and of each component. The direction orthogonal to the axial direction is referred to as a radial direction of the catheter 1 and of each component.

Moreover, an end portion positioned on the distal end side of the catheter 1 and of each component of the catheter 1 is described as a "distal end", and a region including the "distal end" and extending from the distal end to the midway toward the rear end side is described as a "distal end portion". Similarly, an end portion positioned on the rear end side of the catheter 1 and of each component of the catheter 1 is described as a "rear end", and a region including the "rear end" and extending from the rear end to the midway toward the distal end side is described as a "rear end portion".

The catheter 1 is a medical instrument inserted into blood vessels or digestive organs for treatment or examination. The catheter 1 includes a hollow shaft 10, a distal tip 60, and a grip portion 70.

The hollow shaft 10 is a long tubular body extending in the axial direction of the catheter 1. The hollow shaft 10 is formed of flexible resin. The distal end portion of the hollow shaft 10 is curved. The grip portion 70 is connected to the rear end portion of the hollow shaft 10, while the distal tip 60 is connected to the distal end portion of the hollow shaft 10. The lumen (inner cavity) of the hollow shaft 10 is communicated to the lumen of the grip portion 70 and the lumen of the distal tip 60.

The distal tip 60 is a tubular body connected to the distal end portion of the hollow shaft 10. The distal tip 60 is a member forming the most distal end of the catheter 1 to reduce the possibility that the catheter 1 damages an internal body. The distal tip 60 may be formed of a flexible material, e.g., a resin material, e.g., TPU (thermoplastic polyurethane elastomer) or a metal material.

The grip portion 70 is a tubular body connected to the rear end portion of the hollow shaft 10. A user, e.g., a physician, holds the grip portion 70 to operate the catheter 1. The grip portion 70 includes a protector 71, a main body 72, and a connector 73. The protector 71 has a tapered shape with an outer diameter increasing toward the rear end side of the protector 71. The main body 72 has a projection on the outer periphery so as to facilitate holding by a tuser. The connector 73 has a screw thread on the inner peripheral side, and is connectable to another medical device such as a syringe, e.g., the grip portion 70 may be formed of a material that is durabile and suitable for sterilization. For example, metal, resin formed by injection molding, or a combination thereof may be used.

The hollow shaft 10 includes a first hollow shaft 11, a second hollow shaft 12, and a third hollow shaft 13. The proximal end portion of the first hollow shaft 11 is connected to the grip portion 70, and the distal end portion thereof is connected to the second hollow shaft 12. The proximal end portion of the second hollow shaft 12 is connected to the distal end portion of the first hollow shaft 11, and the distal end portion thereof is connected to the third hollow shaft 13. The proximal end portion of the third hollow shaft 13 is connected to the distal end portion of the second hollow shaft 12, and the distal end portion thereof is connected to the distal tip 60. A connection portion 14 is between the distal end of the first hollow shaft 11 and the rear end of the second hollow shaft 12. The connection portion 14 is a linear part of the hollow shaft 10. In other words, the connection portion 14 is on the axis of the first hollow shaft 11. A connection portion 15 is between the distal end of the second hollow shaft 12 and the rear end of the third hollow shaft 13. The first hollow shaft 11 is substantially linear, and is substantially parallel to the axial direction of the catheter 1. At least a part of the second hollow shaft 12 is curved. At least a part of the third hollow shaft 13 is curved. The first hollow shaft 11, the second hollow shaft 12, and the third hollow shaft 13 are continuously connected, and have a lumen in communication with each other. The lumen is used to insert other devices, e.g., a guide wire, feed chemical liquid, and the like.

In the embodiment, in the hollow shaft 10, a first section 21 is a substantially linear section that is formed by the first hollow shaft 11, a second section 22 includes a substantially linear part and a curved portion formed by the second hollow shaft 12, and a third section 23 includes a curved portion formed by the third hollow shaft 13. The length of the first section 21 may be longer than a length of either of the second section 22 and the third section 23. Moreover, the length of the first section 21 may be longer than a total length of the second section 22 and the third section 23 combined.

The rigidity of the first section 21 may be larger than the rigidity of the second section 22. Moreover, the rigidity of the second section 22 may be larger than the rigidity of the third section 23. In the embodiment, the rigidity of the first hollow shaft 11 is larger than the rigidity of the second hollow shaft 12, and the rigidity of the second hollow shaft 12 is larger than the rigidity of the third hollow shaft 13. In other words, the rigidity of the hollow shaft 10 is reduced stepwise from the rear end side toward the distal end side. Thus, the catheter 1 has a configuration in which the flexibility increases toward the distal end direction of the catheter 1. For example, with the rigidity of the third section 23 being 1, the ratio of rigidity among the sections may be third section 23: second section 22: first section 21=1:10 to 20:30 to 300. In this case, the rigidity value of each section may beset to 0.005 to 0.050 gf $cm^2$/cm in the third section 23, 0.050 to 1.00 gf $cm^2$/cm in the second section 22, and 0.150 to 15.0 gf $cm^2$/cm in the first section 21. With the rigidity of each section designed in this manner, the catheter 1 may have pushability and distal flexibility. That is, the inventors have found that in the hollow shaft 10 having a first curved portion 31 and a second curved portion 32, which will be described later, and having a first distance D1, a second distance D2, and a third distance D3 satisfying a condition described later, both the pushability and the distal flexibility are sufficiently satisfied when the rigidity of the first section, the second section, and the third section are set to the above-described range.

A virtual plane 40 is positioned on the axis of the first hollow shaft 11 and extends toward the distal end direction of the catheter 1. The virtual plane 40 in FIG. 1 illustrates a longitudinal section thereof. A first space area 51 extends on a first side of, e.g., above, the virtual plane 40, while a second space area 52 extends on a second side of, e.g., below, the virtual plane 40 is, the space areas being divided and thus defined by the virtual plane 40. The first space area 51 and the second space area 52 face each other with the virtual plane 40 as a boundary.

A first curved portion 31 is part of the curved shape formed by the second hollow shaft 12 in the first area 51 in the second section 22. A second curved portion 32 is part of the curved shape formed by the third hollow shaft 12 in the second area 52 in the third section 23. The connection portion 15 between the second hollow shaft 12 and the third hollow shaft 13 is between the first curved portion 31 and the second curved portion 32.

Figure 2:
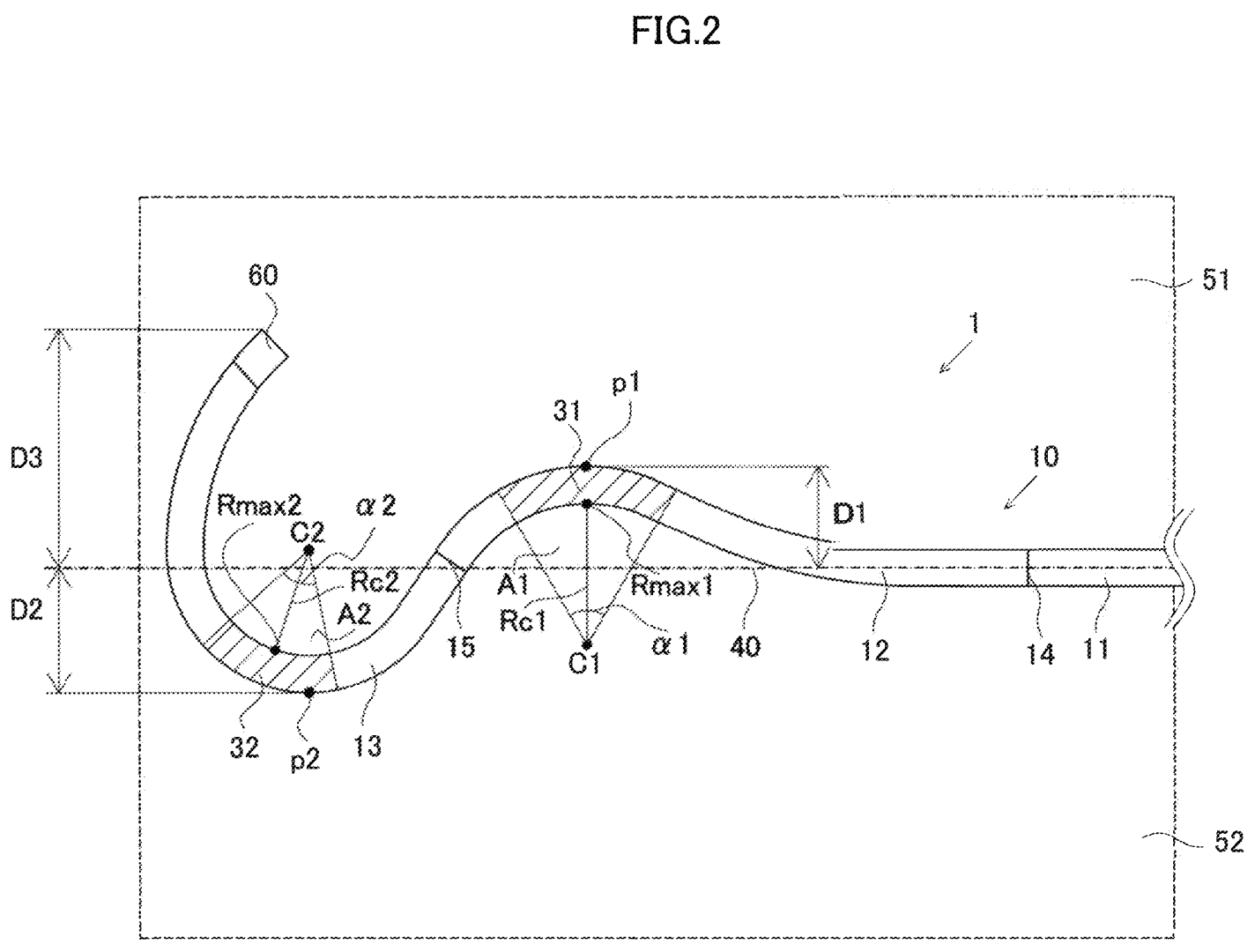

FIG. 2 is an explanatory view illustrating curved portions of the catheter 1 according to the first embodiment.

A part with the largest curvature, in the curved shape formed by the second hollow shaft 12, is a most curved portion Rmax1 having a center C1 of the curvature radius Rc1. The range of the first curved portion 31 in the second hollow shaft 12 is a part included inside an arc A1 with a center angle α1 of 60°, the arc A1 symmetrically expanding on both sides of the curvature radius Rc1 of the most curved portion Rmax1 as a center line from the center C1 toward the outside of the curved shape. A part with the largest curvature, in the curved shape formed by the third hollow shaft 13, is a most curved portion Rmax2 having a center of the curvature radius Rc2. The range of the second curved portion 32 in the third hollow shaft 13 is a part included inside an arc A2 with a center angle α2 of 60°, the arc A2 symmetrically expanding on both sides of the curvature radius Rc2 of the most curved portion Rmax2 as a center line from the center C2 toward the outside of the curved shape. In each figure, the first curved portion 31 and the second curved portion 32 are hatched.

Figure 4:
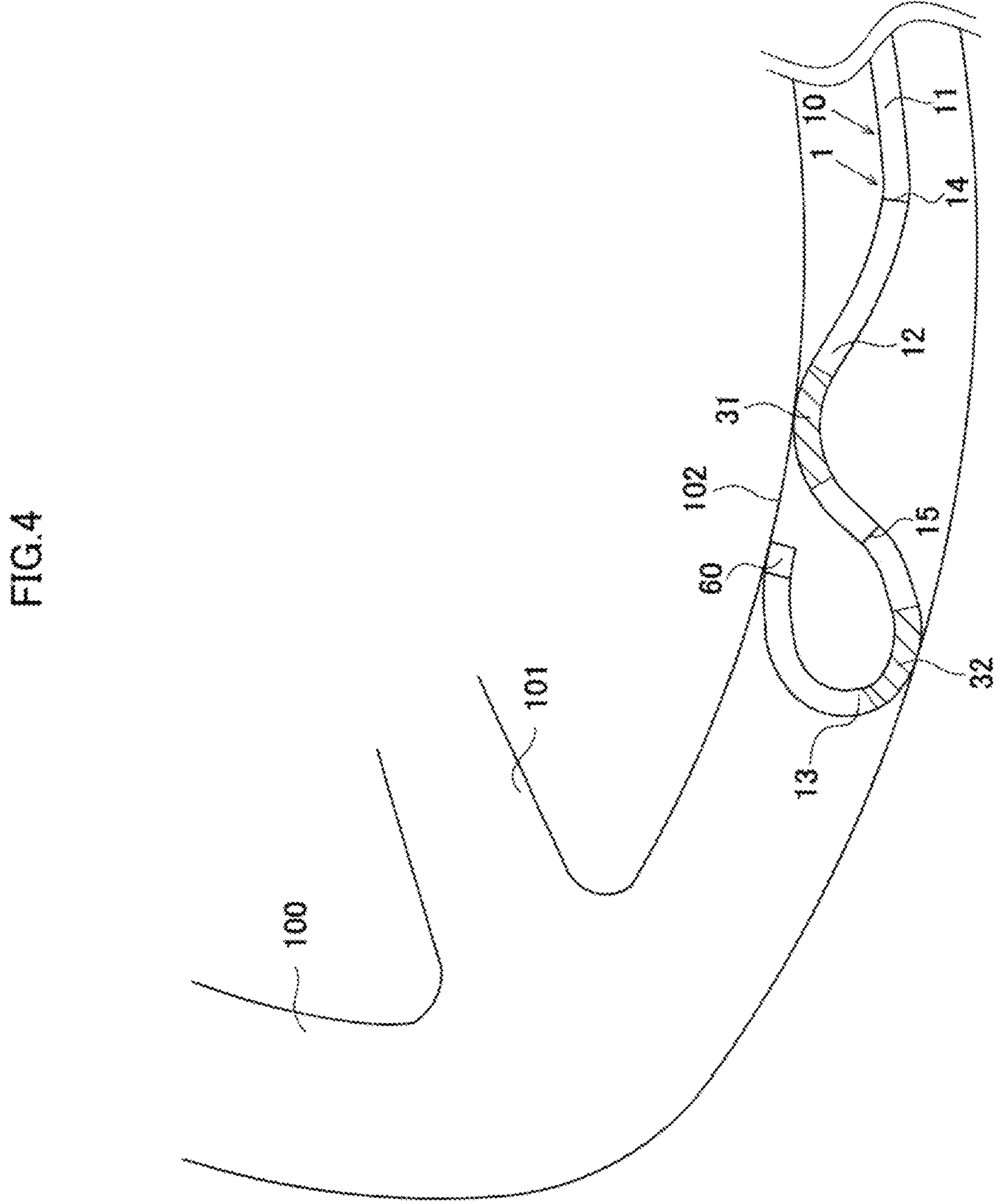
FIG. 4 is a first explanatory view illustrating a use state of the catheter in a blood vessel.

In the first curved portion 31, a vertex p1 of the first curved portion is the point furthest from the virtual plane 40. A distance from the vertex p1 of the first curved portion to the virtual plane 40 is the first distance D1. In the second curved portion 32, a vertex p2 of the second curved portion is the furthest from the virtual plane 40. A distance from the vertex p2 of the second curved portion to the virtual plane 40 is the second distance D2. In the distal end of the catheter 1 (the distal end of the distal tip 60), a distance between the point most apart from the virtual plane 40 and the virtual plane 40 is the third distance D3. In the catheter 1, in a free state, i.e., unbent, the second distance D2 is larger than the first distance D1. Thus, as illustrated in FIG. 4, in a state where the distal end (distal tip 60) of the catheter 1 is bent to the proximal end side of the catheter 1 in a blood vessel, the second distance D2 is shortened, so that the first distance D1 and the second distance D2 become substantially equal. Therefore, force generated when the proximal end side of the catheter 1 is pushed passes the vicinity of the center of gravity on the distal end side of the catheter 1, thereby improving the pushability. Moreover, if the first distance D1 is larger than the second distance D2, the length of the first curved portion 31 is relatively large at the distal end portion of the catheter 1. In this case, force generated when the proximal end side of the catheter 1 is pushed is absorbed by the first curved portion 31 when the first curved portion 31 is bent. With the first distance D1 smaller than the second distance D2 an attenuation rate of force may be reduced until the force generated when the proximal end side of the catheter 1 is pressed reaches the distal end of the catheter 1. In the catheter 1, the third distance D3 is larger than the first distance D1. In this manner, the distal end (distal tip 60) of the catheter 1 may be easily bent to the proximal end side of the catheter 1 in a blood vessel as illustrated in FIG. 4. Moreover, in the catheter 1, the third distance D3 is larger than the second distance D2. In this manner, as illustrated in FIG. 4, in a state where the distal end (distal tip 60) of the catheter 1 is bent to the proximal end side of the catheter 1 in a blood vessel, the reduction amount of the third distance D3 is larger than the reduction amount of the second distance D2, so that the second distance D2 and the third distance D3 become substantially equal. Therefore, force generated when the proximal end side of the catheter 1 is pushed passes the vicinity of the center of gravity on the distal end side of the catheter 1, thereby improving the pushability. Moreover, if the first distance D1 is larger than the third distance D3 the length of the first curved portion 31 is relatively large at the distal end portion of the catheter 1. In this case, force generated when the proximal end side of the catheter 1 is pushed is absorbed by the first curved portion 31 when the first curved portion 31 is bent. With the first distance D1 smaller than the third distance D3, an attenuation rate of force may be reduced until the force generated when the proximal end side of the catheter 1 is pressed reaches the distal end of the catheter 1. For example, with the rigidity of the first distance D1 being 1, the ratio of rigidity among the distances may be first distance D1: second distance D2: third distance D3=1:5 to 10:6 to 16. In this case, the first distance D1 may be set to 0.500 to 3.00 mm, the second distance D2 may be set to 2.50 to 5.00 mm, and the third distance D3 may be set to 3.00 to 8.00 mm.

The most curved portion Rmax2 of the second curved portion is provided on the more distal end side in the axial direction of the catheter 1 than the vertex p2 of the second curved portion. In this manner, the distal end (distal tip 60) of the catheter 1 is preliminarily bent slightly to the proximal end side of the catheter 1. Thus, the distal end of the catheter 1 may more easily bend to the proximal end side of the catheter 1 in a blood vessel as illustrated in FIG. 4.

The maximal curvature of the second curved portion 32 is larger than the maximum curvature of the first curved portion 31. In other words, the maximal curvature of the curved portion on the distal end side is larger than the maximum curvature of the curved portion on the rear end side. Thus, the distal end of the catheter 1 has a shape warping to the rear end side of the catheter 1.

The rigidity of the first curved portion 31 is larger than the rigidity of the second curved portion 32. In other words, the rigidity of the curved portion on the rear end side is larger than the rigidity of the curved portion on the distal end side. In this manner, the distal end of the catheter 1 may be more easily bent to the proximal end side while suppressing deformation of the first curved portion 31 when the distal end (distal tip 60) of the catheter 1 is bent to the proximal end side of the catheter 1. Moreover, an attenuation rate at the first curved portion 31 of force generated when the proximal end side of the catheter 1 is pushed may be reduced.

Figure 3:
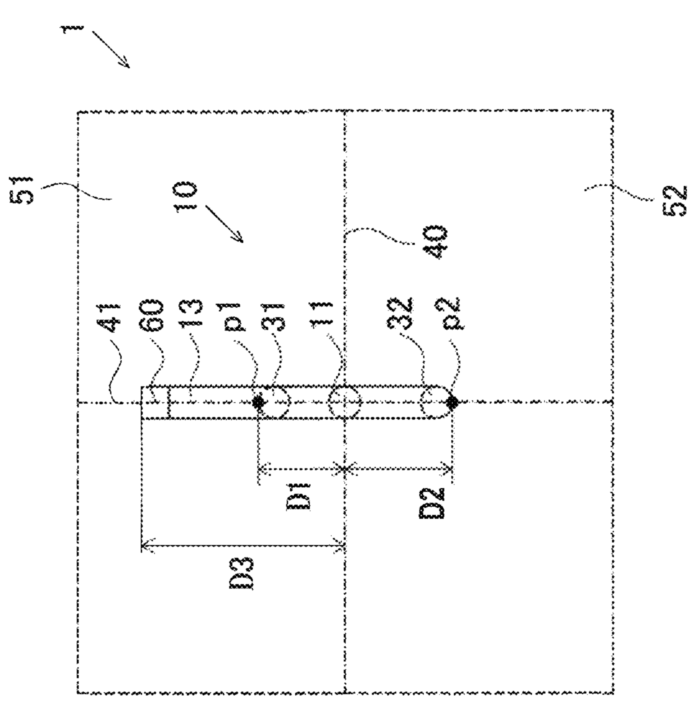
FIG. 3 is an explanatory view illustrating a front view of the catheter according to the first embodiment.

FIG. 3 is an explanatory view illustrating a front view of the catheter according to the first embodiment. FIG. 3 illustrates, with dotted line, the outline of the transverse section of the distal end portion of the first section 21, the outline of the transverse section of the first curved portion 31 including the vertex p1, and the outline of the transverse section of the second curved portion 32 including the vertex p2.

The distal end portion of the first section 21 of the first hollow shaft 11, the vertex p1 of the first curved portion 31 and the vertex p2 of the second curved portion 32, and the distal tip 60 are positioned on one straight virtual line 41. Note that being straight here includes a case of being completely straight and a case of being substantially straight. For example, in the front view of FIG. 3, if an angle formed by a straight line connecting the distal tip 60 and the vertex p2 of the second curved portion 32 and a straight line connecting the vertex p2 of the second curved portion 32 and the vertex p1 of the first curved portion 31 is equal to or smaller than 10°, these are considered to be positioned on a straight line.

The hollow shaft 10 preferably has antithrombogenicity, flexibility, and biocompatibility, and may be formed of a resin material, e.g., polyamide resin, polyolefin resin, polyester resin, polyurethane resin, silicone resin, fluororesin, or the like for example. The outer diameter, the inner diameter, and the length of the hollow shaft 10 may be arbitrarily determined.

FIG. 4 is a first explanatory view illustrating a use state of the catheter 1 in a blood vessel.

In FIG. 4, the catheter 1 is inserted in a blood vessel 100. A user advances the catheter 1 in a blood vessel toward a target region, e.g., a lesion to be treated. In a case where the inner diameter of the blood vessel 100 is smaller than a distance between the first curved portion 31 and the second curved portion 32 of the catheter 1, as illustrated in FIG. 4, both the first curved portion 31 and the second curved portion 32 advance while being in contact with a blood vessel wall 102. Thus, the catheter 1 advances while applying force in the radial direction of the blood vessel 100 with the first curved portion 31 and the second curved portion 32 as contacts. In other words, the catheter 1 advances in the blood vessel 100 while pushing and widening the blood vessel wall 102. A user may advance the catheter 1 in a branching blood vessel 101. In that case, the user pushes or pulls the catheter 1 or rotates the catheter 1 to insert the distal end of the catheter 1 into the branching blood vessel 101.

Examples of the Effects of the First Embodiment

Figure 5:
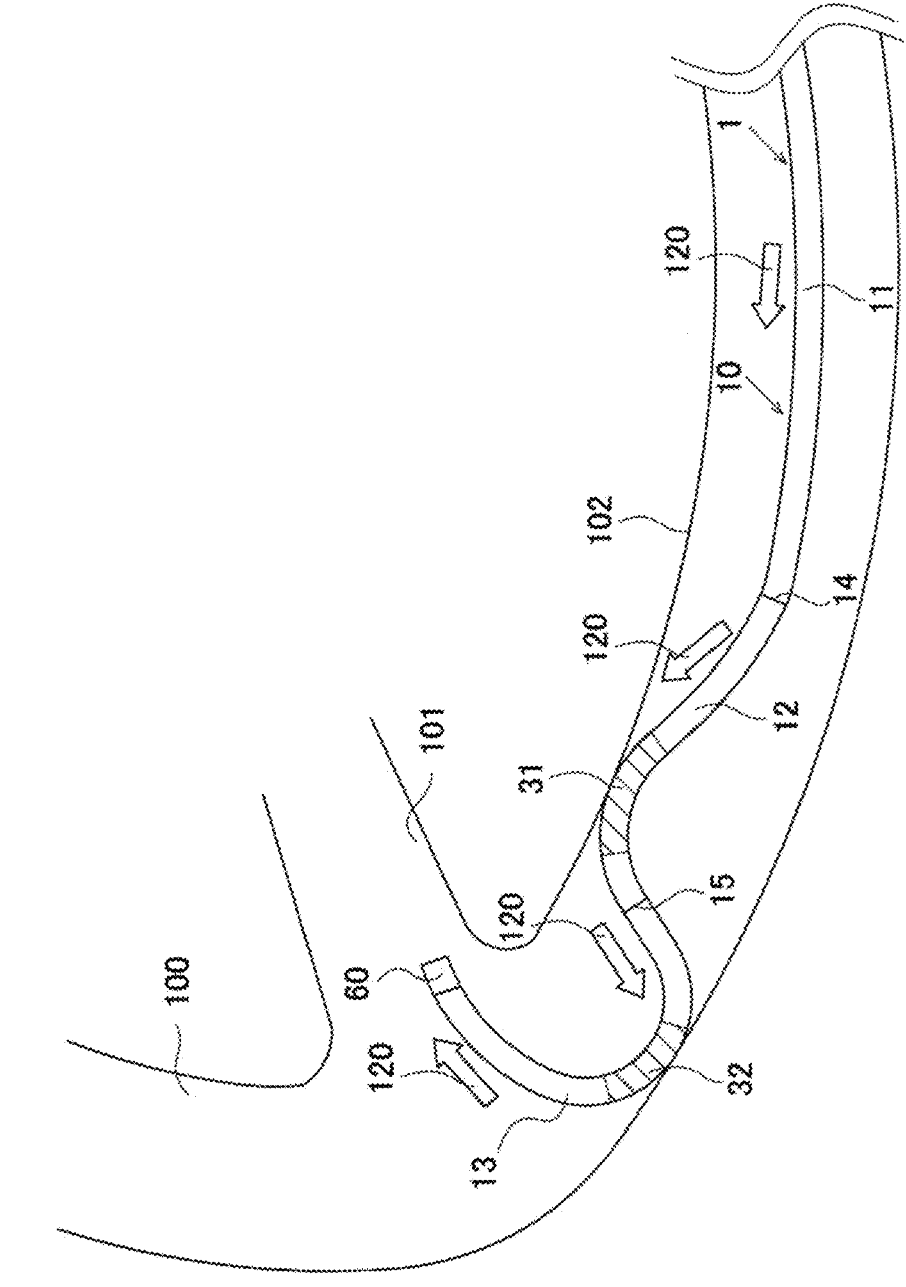
FIG. 5 is a second explanatory view illustrating a use state of the catheter in a blood vessel.

FIG. 5 is a second explanatory view illustrating a use state of the catheter 1 in a blood vessel.

FIG. 5 illustrates the state in which the distal end of the catheter 1 is inserted in the branching blood vessel 101. When a target lesion is in the branching blood vessel 101, a technician such as a physician confirms that the distal end of the catheter 1 is inserted in the branching blood vessel 101, and then advances the catheter 1 into the branching blood vessel 101.

When the catheter 1 is brought to a branching portion of a blood vessel, the distal end of the catheter 1 pressed by the blood vessel wall 102 is released, and the distal end of the catheter 1 tends to restore the original curved shape. Thus, the distal end of the catheter 1 is inserted to the branching blood vessel 101. Therefore, the use is able to easily advance the catheter 1 into the branching blood vessel 101. Moreover, force 120 applied in the axial direction of the catheter 1 by the user pushing in the catheter 1, for example, is transmitted to the distal end of the catheter 1 through the first curved portion 31 and the second curved portion 32. Here, the first curved portion 31 and the second curved portion 32 are supported by the blood vessel wall 102. Thus, the force 120 is converted from the force in the axial direction of the catheter 1 to the force in the distal end direction. Thus, the distal end of the catheter 1 is easily advanced into the branching blood vessel 101.

The catheter 1 advances while pushing and widening the blood vessel 100. In this manner, when force in the opposite direction from the advancing direction of the catheter 1 is applied on the catheter 1, the resistance force acting to prevent the catheter 1 from being pushed back (backup force of the catheter 1) is exerted, thereby reducing the possibility that the catheter 1 is pushed back. Moreover, the rigidity of the first curved portion 31 is larger than the rigidity of the second curved portion 32. Thus, the backup force of the catheter 1 occurs at the first curved portion 31. Therefore, the possibility that the catheter 1 is pushed back in the opposite direction from the advancing direction may be reduced.

The length of the first section is longer than those of the second section and the third section. In this manner, when chemical liquid is injected to the lumen of the catheter 1, and the injected chemical liquid is ejected from the distal end of the catheter 1, the resistance force acting to prevent the catheter 1 from being pushed back (backup performance of the catheter 1) is sufficiently exerted, thereby reducing the possibility that the catheter 1 is pushed back. Moreover, the length of the first section is longer than the total length of the second section and the third section. This further improves the backup performance of the catheter 1.

The rigidity of the first section 21 is larger than the rigidity of the second section 22. Thus, the force for pushing in the catheter 1, the force for rotating the catheter 1, and the like, may be securely transmitted from the rear end side of the catheter 1 to the distal end side of the catheter 1. Therefore, the user may easily operate the catheter 1. Moreover, the rigidity becomes smaller in the order of the first hollow shaft 11, the second hollow shaft 12, and the third hollow shaft 13. Thus, the flexibility of the catheter 1 increases toward the distal end direction of the catheter 1. Therefore, the catheter 1 is easily adapted to the shapes of complicatedly curved internal organs and blood vessels.

The connection portion 14 between the first hollow shaft 11 and the second hollow shaft 12 is provided at the linear part of the hollow shaft 10. If the connection portion 14 is provided at a curved portion, smooth deformation of the curved portion may be suppressed. With the connection portion 14 provided at the linear part, the possibility that the deformation of the curved portion is suppressed may be reduced.

The connection portion 15 between the second hollow shaft 12 and the third hollow shaft 13 is provided between the first curved portion 31 and the second curved portion 32. If the connection portion 15 is provided at a curved portion, smooth deformation of the curved portion may be suppressed. With the connection portion 15 provided at the linear part, the possibility that the deformation of the curved portion is suppressed may be reduced.

The third distance D3 may be larger than the first distance D1. In other words, the distal end of the catheter 1 is positioned on the outer side in the radial direction of the catheter 1 than the vertex p1 of the first curved portion 31. Thus, when the catheter 1 reaches the branching blood vessel 101, the distal end of the catheter 1 is smoothly inserted to the entrance of the branching blood vessel 101.

The most curved portion Rmax2 of the second curved portion is provided on the more distal end side in the axial direction of the catheter 1 than the vertex p2 of the second curved portion. In this manner, when the catheter 1 advances in the blood vessel 100, the possibility that resistance force occurs against the force applied in the advancing direction of the catheter 1 by a user, is reduced, whereby the catheter 1 easily advances in a blood vessel.

The degree of curvature of the second curved portion 32 is larger than the degree of curvature of the first curved portion 31. Thus, the distal end of the catheter 1 has a shape warping to the rear end side of the catheter 1. Therefore, it becomes easy to advance the distal end of the catheter 1 into the branching blood vessel 101 extending in the opposite direction from the advancing direction of the catheter 1, such as the branching blood vessel 101 illustrated in FIGS. 4 and 5.

As illustrated in FIG. 3, the first hollow shaft 11, the first curved portion 31, and the second curved portion 32 are positioned on one straight virtual line 41. In this manner, as compared with the case where the first hollow shaft 11, the first curved portion 31, and the second curved portion 32 are not arranged on one axis, the possibility that force in a direction orthogonal to the axial direction of the catheter 1 occurs, is reduced. This reduces the possibility that the distal end portion of the catheter 1 rotates in a direction not intended by a user.

Second Embodiment

Figure 6:
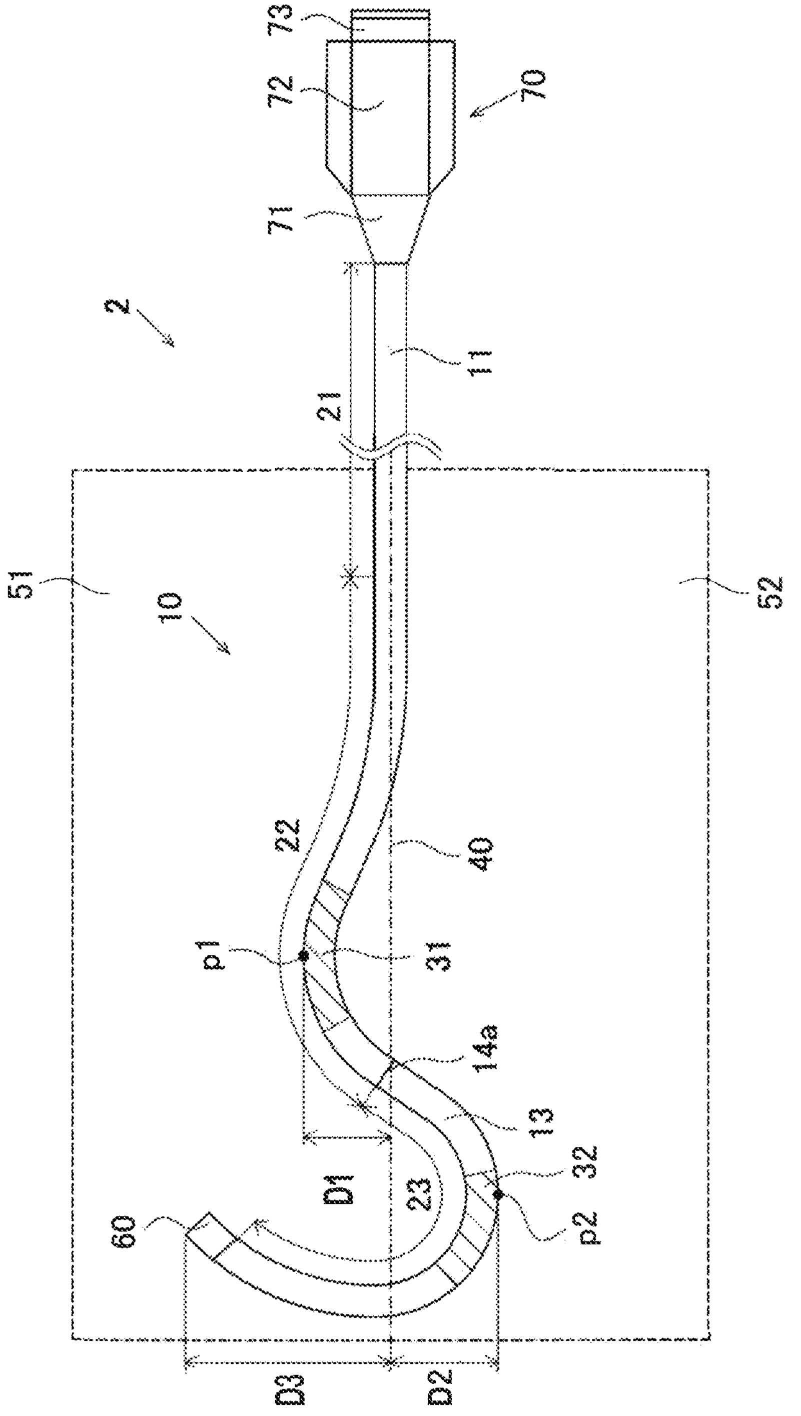
FIG. 6 is an explanatory view illustrating the entire configuration of a catheter according to a second embodiment.

FIG. 6 is an explanatory view illustrating the entire configuration of a catheter according to a second embodiment.

A catheter 2 of the second embodiment is different from the catheter 1 of the first embodiment only in the aspect that the first section 21 and the second section 22 are formed by the first hollow shaft 11 and the first hollow shaft 11 is connected to the third hollow shaft 13. The other parts have the same configurations as the catheter 1, and thus the description thereof is omitted.

In the catheter 2, the first hollow shaft 11 has a part extending substantially linearly from the rear end portion of the catheter 2 toward the distal end direction of the catheter 2, and the first curved portion 31. The distal end portion of the first hollow shaft 11 is connected to the third hollow shaft 13. The rear end portion of the third hollow shaft 13 is connected to the first hollow shaft 11. In other words, the distal end portion of the catheter 2 is formed by two hollow shafts. The first section 21 is defined by the linear part of the first hollow shaft 11. The second section 22 is defined by the linear part of the first hollow shaft 11 and a part including the first curved portion 31. A connection portion **14*a* is between the distal end of the first hollow shaft 11 and the rear end of the third hollow shaft 13**.

Examples of the Effects of the Second Embodiment

In addition to the effects of the catheter 1 of the first embodiment, the catheter 2 avoids stress concentration at the connection portion of a hollow shaft and a hollow shaft and reduces the possibility of a kink by reducing the number of hollow shafts forming the distal end portion of the catheter 2.

Modification Examples of the Embodiments

The disclosed embodiments are not limited to the above-described embodiments, and can be implemented in various aspects without departing from the gist thereof. For example, the following modification examples are also possible.

Modification Example 1

The catheter 1 of the first embodiment may be formed by a multilayer tube in which a plurality of resin tubes are stacked in a radial direction. In this case, the catheter 1 may include, between a plurality of resin layers, a braided body formed by metal wire or a reinforcing body such as a coil body. The catheter 1 may include a plurality of lumens. In that case, one lumen may be used for insertion of a device used together such as a guide wire, and the other lumen may be used for feeding of chemical liquid. Moreover, the catheter 1 may not include the distal tip 60 or the grip portion 70.

Modification Example 2

The hollow shaft 10 of the catheter 1 of the first embodiment may be formed by one resin tube. In this case, the rear end side of one resin tube is formed straight, and the first curved portion 31 and the second curved portion 32 are provided on the distal end side. The hollow shaft 10 may be formed by a plurality of unlimited number of resin tubes connected to each other. In this case, in a plurality of resin tubes, a resin tube positioned on the distal end side includes the first curved portion 31 and the second curved portion 32.

Modification Example 3

The first section 21 and the second section 22 of the catheter 1 of the first embodiment may include a curved portion on the rear end side than the first curved portion 31. In other words, the catheter 1 may include three or more curved portions in a range not losing the effects of the disclosed embodiments.

The above-described modification examples are applicable not only to the first embodiment but also to the second embodiment.

In the above, the present aspects are described on the basis of the embodiments and the modification examples. However, the embodiments of the aforementioned aspects are provided to facilitate understanding of the present aspects, and do not limit the present aspects. The present aspects may be altered or improved without departing from the spirit thereof and claims, and the present aspects include their equivalents. In addition, if the technical features are not described as essential in the present specification, they may be deleted as appropriate.

REFERENCE SIGNS LIST

1 catheter
10 hollow shaft
11 first hollow shaft
12 second hollow shaft
13 third hollow shaft
14 connection portion between first hollow shaft and second hollow shaft
15 connection portion between second hollow shaft and third hollow shaft
21 first section
22 second section
23 third section
31 first curved portion
32 second curved portion
p1 vertex of first curved portion
p2 vertex of second curved portion
40 virtual plane
41 virtual line
51 first area
52 second area
60 distal tip
70 grip portion
71 protector
72 main body
73 connector
100 blood vessel
101 branching blood vessel

102 blood vessel wall

D1 first distance (distance from the vertex of the first curved portion to the virtual plane)

D2 second distance (distance from the vertex of the second curved portion to the virtual plane)

D3 third distance (distance from the distal end of the hollow shaft to the virtual plane)

C1 center of curvature radius Rc1 of the most curved portion Rmax1

C2 center of curvature radius Rc2 of the most curved portion Rmax2

What is claimed is:

1. A catheter, comprising:

a hollow shaft, wherein a distal end portion of the hollow shaft includes a first section extending substantially linearly, a second section at a distal end side of the first section and including a first curved region, and a third section at a distal end side of the second section and including a second curved region, a rigidity of the second section is larger than a rigidity of the third section, with the rigidity of the third section being 1, a ratio of rigidity among the third section, the second section, and the first section is 1:10 to 20:30 to 300, a virtual plane set along an axis of the first section, a first space on a first side with respect to the virtual plane being a first area, and a second space on a second side being a second area, the first curved region and a distal tip of the catheter are in the first area, the second curved region is in the second area, a distance from the distal tip of the catheter to the virtual plane is larger than a distance from a vertex of the first curved region to the virtual plane, and a maximal curvature of the second curved region is larger than a maximum curvature of the first curved region.

2. The catheter according to claim 1, wherein a rigidity of the first section of the hollow shaft is larger than the rigidity of the second section.

3. The catheter according to claim 2, wherein in a front view of the catheter, a distal end of the first section, a vertex of the first curved region, and a vertex of the second curved region in the hollow shaft are arranged on a straight line.

4. The catheter according to claim 1, wherein in a front view of the catheter, a distal end of the first section, a vertex of the first curved region, and a vertex of the second curved region in the hollow shaft are arranged on a straight line.

5. The catheter according to claim 1, wherein a length of the first section is greater than a length of either of the second and third sections.

6. The catheter according to claim 1, wherein a length of the first section is greater than a combined length of both the second and third sections.

7. The catheter according to claim 1, wherein the distance from the vertex of the first curved region to the virtual plane is smaller than a distance from the vertex of the second curved region to the virtual plane.

8. The catheter according to claim 1, wherein the distance from the distal tip of the catheter to the virtual plane is larger than a distance from a vertex of the second curved region to the virtual plane.

9. The catheter according to claim 1, wherein a most curved portion of the second curved region is on the more distal end side in the axial direction than a vertex of the second curved region.

10. The catheter according to claim 1, wherein the first section is a first hollow shaft, the second section is a second hollow shaft, and the third section is a third hollow shaft.

11. The catheter according to claim 10, wherein a first connection between the first hollow shaft and the second hollow shaft is in a first linear region.

12. The catheter according to claim 11, wherein a second connection between the second hollow shaft and the third hollow shaft is in a second linear region.

13. The catheter according to claim 1, wherein the first section and the second section are in a first hollow shaft and the third section is in a second hollow shaft.

14. The catheter according to claim 13, wherein a connection between the first hollow shaft and the second hollow shaft is in a linear region.

15. The catheter according to claim 1, wherein with the distance from the vertex of the first curved region to the virtual plane being 1, a ratio of distances among (a) the distance from the vertex of the first curved region to the virtual plane, (b) a distance from a vertex of the second curved region to the virtual plane, and (c) the distance from the distal tip of the catheter to the virtual plane is 1:5 to 10:6 to 16.

16. A catheter, comprising:

a hollow shaft, wherein a distal end portion of the hollow shaft includes a first section extending substantially linearly, a second section at a distal end side of the first section and including a first curved region, and a third section at a distal end side of the second section and including a second curved region, a rigidity of the second section is larger than a rigidity of the third section, a virtual plane set along an axis of the first section, a first space on a first side with respect to the virtual plane being a first area, and a second space on a second side being a second area, the first curved region and a distal tip of the catheter are in the first area, the second curved region is in the second area, a distance from the distal tip of the catheter to the virtual plane is larger than a distance from a vertex of the first curved region to the virtual plane, a maximal curvature of the second curved region is larger than a maximum curvature of the first curved region, and with the distance from the vertex of the first curved region to the virtual plane being 1, a ratio of distances among (a) the distance from the vertex of the first curved region to the virtual plane, (b) a distance from a vertex of the second curved region to the virtual plane, and (c) the distance from the distal tip of the catheter to the virtual plane is 1:5 to 10:6 to 16.

* * * * *